United States Patent
Yamamoto et al.

(10) Patent No.: US 9,314,380 B2
(45) Date of Patent: Apr. 19, 2016

(54) CONTINUOUS WEB PROCESSING DEVICE

(75) Inventors: Hiroki Yamamoto, Kagawa (JP); Kenji Takeuchi, Kagawa (JP); Fumihito Kawazu, Kagawa (JP)

(73) Assignee: Unicharm Corporation, Ehime (JP)

( * ) Notice: Subject to any disclaimer, the term of this patent is extended or adjusted under 35 U.S.C. 154(b) by 728 days.

(21) Appl. No.: 13/637,150

(22) PCT Filed: Mar. 25, 2011

(86) PCT No.: PCT/JP2011/057292
§ 371 (c)(1),
(2), (4) Date: Nov. 20, 2012

(87) PCT Pub. No.: WO2011/118751
PCT Pub. Date: Sep. 29, 2011

(65) Prior Publication Data
US 2013/0059714 A1    Mar. 7, 2013

(30) Foreign Application Priority Data
Mar. 25, 2010  (JP) ................................. 2010-069799

(51) Int. Cl.
*B31F 1/00* (2006.01)
*A61F 13/15* (2006.01)
*B65H 45/09* (2006.01)

(52) U.S. Cl.
CPC .......... *A61F 13/15747* (2013.01); *B65H 45/09* (2013.01); *B65H 2801/57* (2013.01)

(58) Field of Classification Search
CPC ................ A41B 9/00; A61F 13/15747; A61F 13/15772; A61F 13/49061; A61F 13/15804; A61F 13/15699; A61F 13/496; A61F 13/15764; A61F 13/49; A61F 13/15585; A61F 13/56; A61F 13/5622; A61F 13/565; B29L 2031/4878; B65G 47/32; B65G 47/84; B65B 63/045; B65H 45/09; B65H 45/223; B65H 2801/57; B65H 23/038; B31F 1/10; B32B 2555/02; Y10T 156/1015; Y10T 156/1051; Y10T 156/1343

USPC .............................. 493/442, 5, 356, 364, 410
See application file for complete search history.

(56) References Cited

U.S. PATENT DOCUMENTS 4,666,423 A * 5/1987 Herrington .................... 493/394
7,632,366 B2 * 12/2009 Shimizu et al. ................. 156/64
(Continued)

FOREIGN PATENT DOCUMENTS

CN   1807083 A   7/2006
EP   1 504 738 A2   2/2005
(Continued)

OTHER PUBLICATIONS

Japanese Official Action from corresponding Japanese Application No. JP-2010-069799 mailed on Nov. 19, 2013 (5 pgs).
(Continued)

*Primary Examiner* — Hemant M Desai
*Assistant Examiner* — Valentin Neacsu
(74) *Attorney, Agent, or Firm* — Brinks Gilson & Lione

(57) ABSTRACT

A continuous web processing device including a folding unit that extends in a conveyance direction. The folding unit has a central guide that comes into contact with the bottom of the crotch part of an absorbent article being processed, a pair of side guides that come into contact with the front waistline portion and the rear waistline portion of the absorbent article, and a superimposing roller that superimposes the front waistline portion and the rear waistline portion one on the other. A spacing between the pair of side guides becomes narrower in the downstream conveyance direction. Ends of the side guides are located further upstream than an end of the central guide. The superimposing roller superimposes the front waistline portion and the rear waistline portion of the absorbent article one on the other downstream from the side guides.

6 Claims, 5 Drawing Sheets

(56) References Cited

U.S. PATENT DOCUMENTS

2002/0174930 A1* 11/2002 Umebayashi et al. ....... 156/62.6
2005/0026760 A1* 2/2005 Yamamoto et al. ............. 493/81
2009/0194218 A1* 8/2009 Torstensson et al. ........... 156/64
2010/0168708 A1 7/2010 Umebayashi et al.

FOREIGN PATENT DOCUMENTS

| JP | S61-62018 | 4/1986 |
| JP | 2003-038566 A | 2/2003 |
| WO | WO 01/72237 A2 | 10/2001 |
| WO | WO 2008/142946 A1 | 11/2008 |

OTHER PUBLICATIONS

Chinese Official Action and English translation from corresponding Chinese Application No. 201180015833.X mailed on Jan. 17, 2014 (8 pgs).
European extended Search Report from corresponding European Application No. 11759555.3 dated Mar. 31, 2014 (6 pgs).
Chinese Second Office Action and English translation from corresponding Chinese Application No. 201180015833.X dated Aug. 20, 2014 (15 pgs).
International Search Report based on corresponding PCT application No. PCT/JP_2011/057292 dated Jun. 14, 2011 (4 pgs).

* cited by examiner

FIG. 5
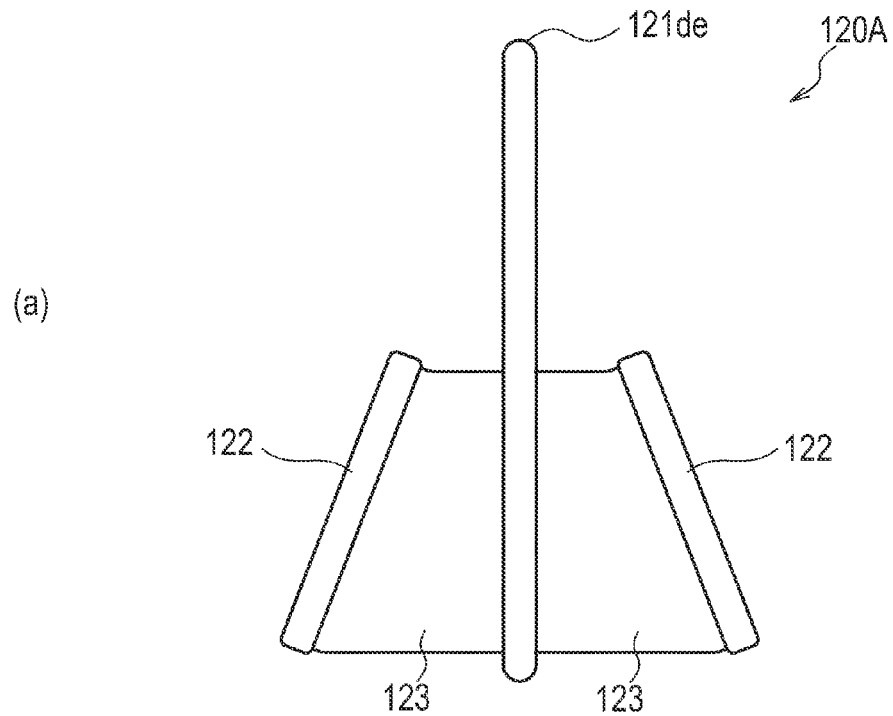
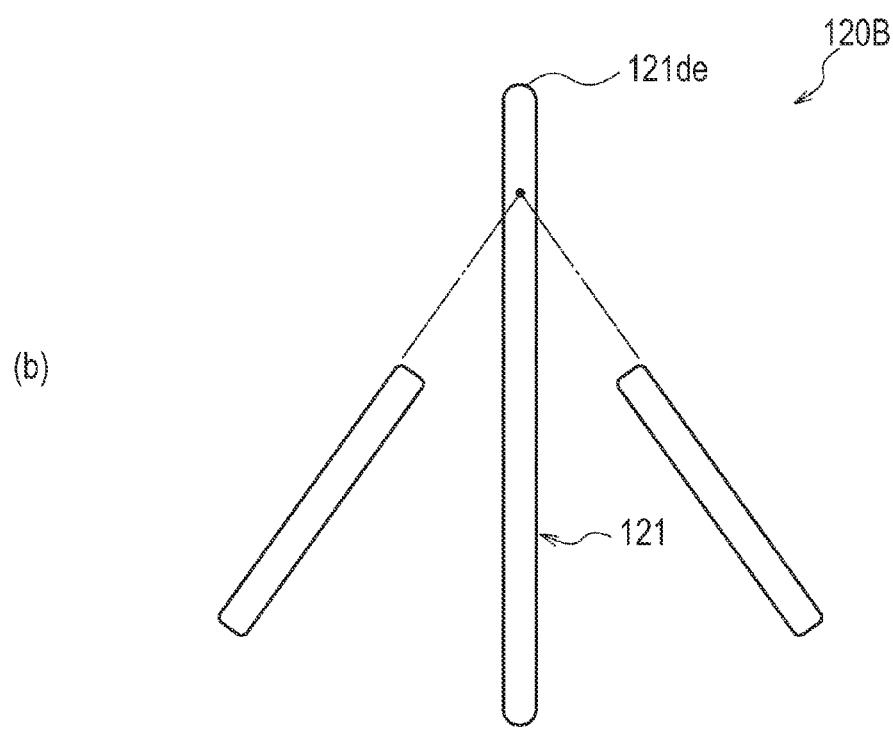

CONTINUOUS WEB PROCESSING DEVICE

RELATED APPLICATION

This application is a 35 U.S.C. §371 national phase filing of International Patent Application No. PCT/JP2011/057292 filed Mar. 25, 2011, to which priority is claimed under 35 U.S.C. §120 and through which priority is claimed under 35 U.S.C. §119 to Japanese Patent Application No. 2010-069799, filed Mar. 25, 2010.

TECHNICAL FIELD

The present invention relates to a continuous web processing device which conveys a continuous web having a front waistline portion, a rear waistline portion, and crotch portion having leg-hole openings formed therein alternatingly, while superimposing the front waistline portion and the rear waistline portion.

BACKGROUND ART

Conventionally, in a manufacturing process for a disposable worn article such as a pant-type disposable diaper having a front waistline portion, a rear waistline portion, and crotch portion having leg-hole openings formed therein, a continuous web processing device, which superimposes the front waistline portion and the rear waistline portion of the continuous web as a half-finished product, has been widely used. With such a continuous web processing device, generally, the continuous web is folded in two by superimposing the front waistline portion and the rear waistline portion on each other based on a part which turns into the crotch portion (for example, Patent Literature 1).

CITATION LIST

Patent Literature

[Patent Literature 1] Japanese Patent Publication No. 2003-38566 (Page 4, FIG. 2)

SUMMARY OF INVENTION

However, the continuous web processing device described above has the following problems. That is, in a case where the continuous web having the leg-hole openings formed therein alternatingly is folded in two while being conveyed, the force exerted to pull the front waistline portion and the rear waistline portion toward the crotch portion side is greatly changed based on the presence or absence of the crotch portion which is alternatingly provided on the continuous web.

Therefore, superimposition between the front waistline portion and the rear waistline portion becomes unstable, thereby leading to a problem that it is difficult to assure the quality of the manufactured disposable worn article. For example, this makes it easier for an elastic member (rubber thread) provided in the front waistline portion, the rear waistline portion, or the like, to be displaced from a predetermined position. Further, unless edges of the superimposed front and rear waistline portions correspond to each other, the edge of one of waistline portions comes in contact with the skin of a wearer, thereby easily giving feeling of discomfort.

The present invention has been achieved in consideration of such circumstances, and an object thereof is to provide a continuous web processing device, by which in a case where a continuous web having a front waistline portion, a rear waistline portion, and crotch portion having leg-hole openings formed therein alternatingly is folded in two while being conveyed, a quality of products can be prevented from deteriorating due to the fact that superimposition between the front waistline portion and the rear waistline portion becomes unstable.

A feature of the present invention is summarized as a continuous web processing device (processing device 100) configured to convey a continuous web having a front waistline portion (front waistline portion 11), a rear waistline portion (rear waistline portion 12), and a crotch portion (crotch portion 13), while superimposing the front waistline portion and the rear waistline portion, the crotch portion being formed between the front waistline portion and the rear waistline portion and having leg-hole openings (leg-hole openings 14) formed in the crotch portion alternatingly in a conveyance direction. The continuous web processing device comprising: a folding base unit (folding base unit 110) configured to come in contact with one face of the continuous web and change the conveyance direction of the continuous web from a first conveyance direction (MD1) to a second conveyance direction (MD2) in which the first conveyance direction intersects with a face of the continuous web; and a folding unit (folding unit 120) configured to superimpose the front waistline portion and the rear waistline portion, wherein: the folding unit has: a central guiding unit (central guiding unit 121) configured to extend in the second conveyance direction downstream from the folding base unit, and to come in contact with the crotch portion; a pair of side guiding units (side guiding units 122) configured to come in contact with the front waistline portion and the rear waistline portion; and a superimposing unit (superimposing roller 150) configured to superimpose the front waistline unit and the rear waistline unit; an interval (interval V1) between the pair of side guiding units becomes shorter as the side guiding units extend downstream; downstream ends 122de of the side guiding units are positioned upstream from the downstream from the downstream end of the central guiding unit 121de; and the superimposing unit superimposes the front waistline portion and the rear waistline portion, downstream from the side guiding units.

According to one characteristic of the present invention, it is possible to provide a continuous web processing device, by which in a case where a continuous web having a front waistline portion, a rear waistline portion, and crotch portion having leg-hole openings formed therein alternatingly is folded in two while being conveyed, a quality of products can be prevented from deteriorating due to the fact that superimposition between the front waistline portion and the rear waistline portion becomes unstable.

BRIEF DESCRIPTION OF DRAWINGS

FIGS. 5(a) and 5(b) are views each showing a folding unit 120A and a folding unit 120B according to a modification of the present invention.

DESCRIPTION OF EMBODIMENT

Figure 1:
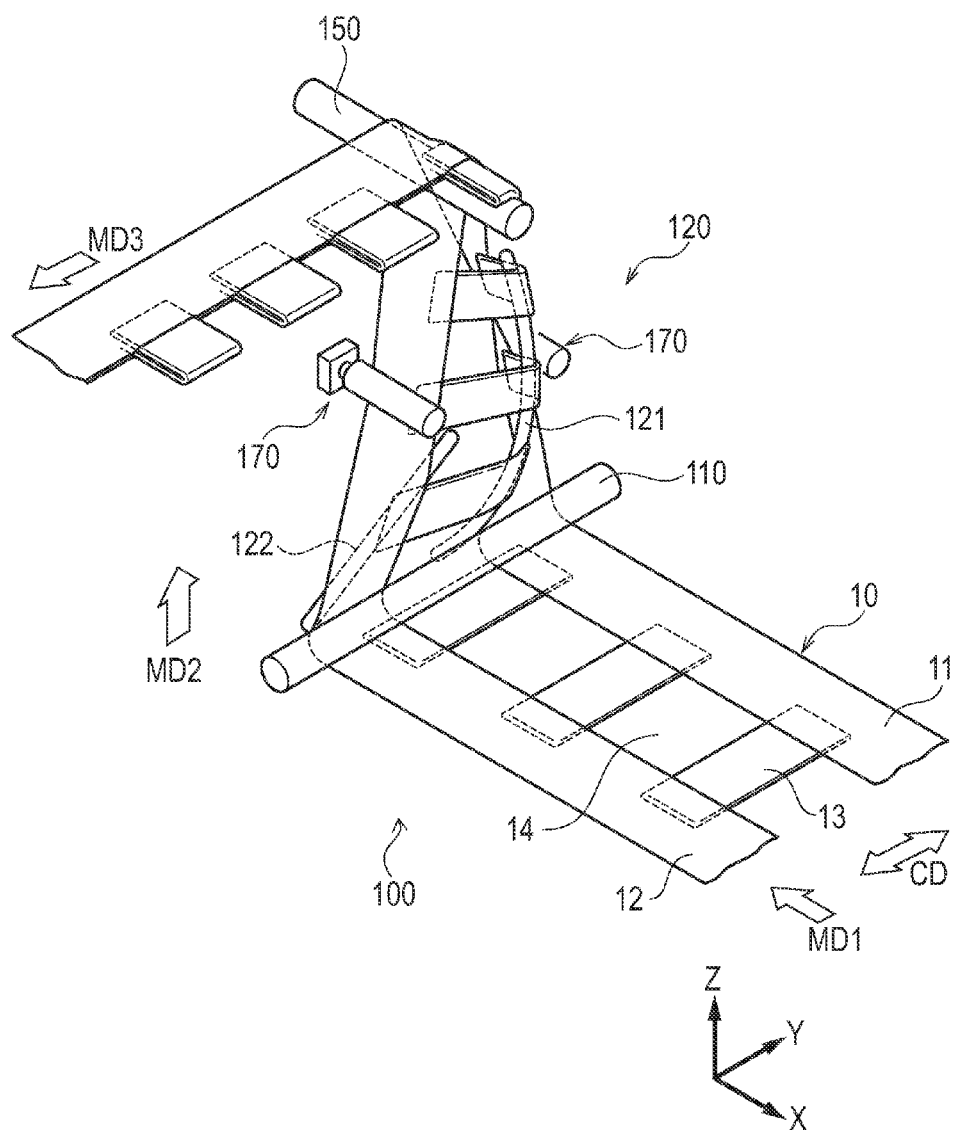
FIG. 1 is a perspective view showing an entire configuration of a processing device 100 according to an embodiment of the present invention.

Next, an embodiment of a continuous web processing device according to the present invention is explained with reference to drawings. In the following description of the drawings, the same or similar reference numerals are used to designate the same or similar parts. It will be appreciated that the drawings are schematically shown and the ratio and the like of each dimension are different from the real ones.

A specific dimension should be determined in view of the following description. Further, among the drawings, the respective dimensional relations or ratios may naturally differ.

(1) Entire Schematic Configuration of Continuous Web Processing Device

FIG. 1 is a perspective view showing an entire schematic configuration of a continuous web processing unit 100 (hereinafter, abbreviated as a processing device 100) according to the present embodiment. The processing device 100 is used for manufacturing a pant-type disposable diaper. A continuous web 10 is made of a continuous body of material such as a nonwoven fabric, a resin film, or the like, and has a front waistline portion 11 corresponding to a front waistline of a wearer, a rear waistline portion 12 corresponding to a rear waistline of the wearer, and crotch portion 13 formed between the front waistline portion 11 and the rear waistline portion 12. In the crotch portion 13, leg-hole openings 14 are formed alternatingly.

The continuous web 10 is conveyed by a conveyance device (belt conveyor) not shown. In the present embodiment, a direction in which the continuous web 10 is conveyed is defined as a conveyance direction, and the conveyance direction is indicated as "MD1 to MD3" in the drawings. Further, a direction which extends along a face of the continuous web 10 and is orthogonal to the conveyance direction is defined as a crossing direction, and is indicated as "CD" in the drawings.

The processing device 100 changes the conveyance direction of the continuous web 10, in order of MD1, MD2, and MD3, while conveying and folding the continuous web 10 in two. The leg-hole opening 14 is a space formed between the crotch portion 13, and is formed alternatingly in the conveyance direction of the continuous web 10.

The processing device 100 has a folding base unit 110, a folding unit 120, and a superimposing roller 150. Note that, as described above, the continuous roller 10 is conveyed by a conveyance device (belt conveyor), not shown, up to the folding base unit 110 and also downstream from the superimposing roller 150.

The folding base unit 110 comes in contact with one face of the continuous web 10, in particular, a rear face side of an absorber (not shown) provided in the crotch portion 13, and changes the conveyance direction of the continuous web 10. Specifically, the folding base unit 110 changes the conveyance direction of the continuous web 10 from MD1 (first conveyance direction) to MD2 (second conveyance direction) in which the MD1 intersects with a face (face YZ) of the continuous web. In the present embodiment, the MD1 (direction X) and the MD2 (direction Z) are different by approximately 90 degrees. The MD1 extends in the horizontal direction, whereas the MD2 extends in the vertical direction.

The folding base unit 110 is a cylindrical member, and the continuous web 10 slides in contact with the outer circumferential surface of the folding base unit 110. It is preferable that a width in the crossing direction (CD) of the folding base unit 110 be larger than a width in the crossing direction of the continuous web 10.

Note that it is preferable that the outer circumferential surface of the folding base unit 110 be subjected to the process for reducing friction with the continuous web 10 (for example, fluorine coating). Further, in the present embodiment, the folding base unit 110 is fixed without rotating. However, the folding base unit 110 may be supported rotatably.

The folding unit 120 superimposes the front waistline portion 11 and the rear waistline portion 12 which are conveyed in the vertical direction. Specifically, the folding unit 120 is located downstream from the folding base unit 110. The folding unit 120 comes in contact with the continuous web 10, and folds the continuous web 10 in two based on the center of the crotch portion 13 in the crossing direction.

The folding unit 120 has a central guiding unit 121 and a pair of right and left side guide units 122. The central guiding unit 121 and the side guiding units 122 come in contact with the conveyed continuous web 10. The continuous web 10 is caused to pass in contact with the central guiding unit 121 and the side guiding units 122, thereby being folded in two based on the center of the crotch portion 13 in the crossing direction. As a result, the front waistline portion 11 and the rear waistline portion 12 are superimposed on each other.

The central guiding unit 121 extends in the direction MD2 (direction Z) downstream from the folding base unit 110. The central guiding unit 121 comes in contact with the crotch portion 13. The pair of right and left side guiding units 122 comes in contact with the front waistline portion 11 and the rear waistline portion 12. In the present embodiment, the central guiding unit 121 and the side guiding units 122 comprise a rod shaped member. The central guiding unit 121 and the side guiding units 122 are fixed by means of a support or the like, not shown. The central guiding unit 121 and the side guiding units 122 can be made from a metal, a synthetic resin, or the like. Further, it is preferable that surfaces of the central guiding unit 121 and the side guiding units 122 be subjected to the process for reducing friction with the continuous web 10.

In the present embodiment, the folding unit 120 has an automatic positioning mechanism 170. The automatic positioning mechanism 170 adjusts a position of one face of the continuous web 10 which the folding unit 120 is about to fold, specifically, a position of a face of the front waistline portion 11 or the rear waistline portion 12. Details of the automatic positioning mechanism 170 are described later.

The superimposing roller 150 is provided downstream from the folding unit 120. The superimposing roller 150 rotates in contact with one face (the rear waistline portion 12) of the continuous web 10 folded in two, and changes the conveyance direction of the continuous web 10. Specifically, the superimposing roller 150 changes the conveyance direction of the continuous web 10 from the MD2 to the MD3. In the present embodiment, the MD2 (direction Z) and the MD3 (direction Y) are different by approximately 90 degrees. The MD3 extends in the horizontal direction.

That is, the superimposing roller 150 changes the conveyance direction of the continuous web 10 in which the front waistline portion 110 and the rear waistline portion 12 are superimposed on each other, from the MD2 to the MD3 as a direction orthogonal to the MD2, when viewed in the direction (direction X) orthogonal to the face (face YZ) of the continuous web 10 to be conveyed in the MD2 (second conveyance direction). Note that in FIG. 1, although the conveyance direction is changed so that the front waistline portion 11 is positioned on the top side, the conveyance direction may be changed to the opposite direction of the MD3 so that the rear waistline portion 12 is positioned on the top side.

Further, the superimposing roller 150 superimposes the front waistline portion 11 and the rear waistline portion 12 on each other while changing the conveyance direction of the continuous web 10 from the MD2 to the MD3 as described above. In the present embodiment, the superimposing roller 150 configures a superimposing unit. The superimposing roller 150 superimposes the front waistline unit 11 and the rear waistline unit 12 on each other downstream side from the central guiding unit 121 of the folding unit 120. Note that the superimposing roller 150 may not necessarily be provided downstream from the central guiding unit 121 of the folding unit 120, as long as the superimposing roller 150 is provided downstream from the side guiding units 122 of the folding unit 120.

(2) Configuration of Folding Unit 120

Figure 2:
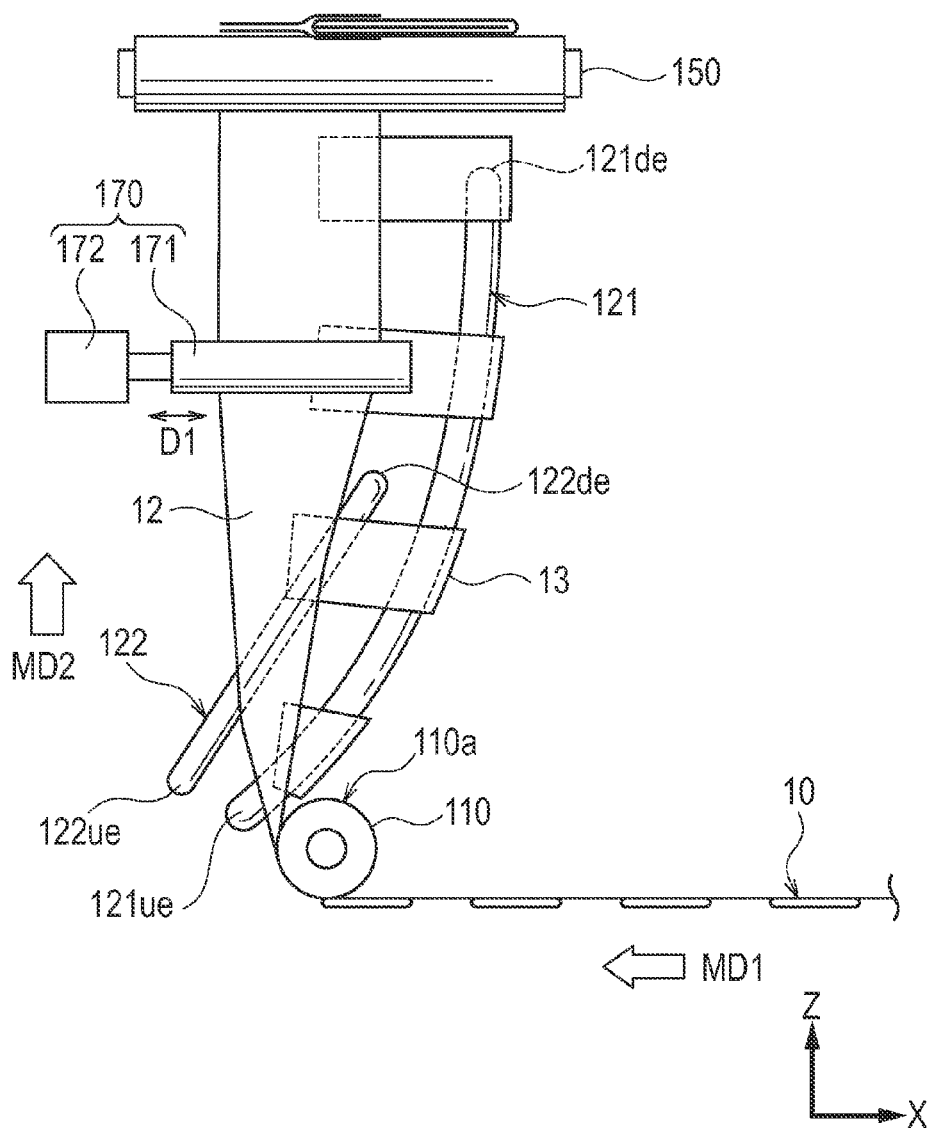
FIG. 2 is a side view showing a folding unit 120 according to the embodiment of the present invention.
Figure 3:
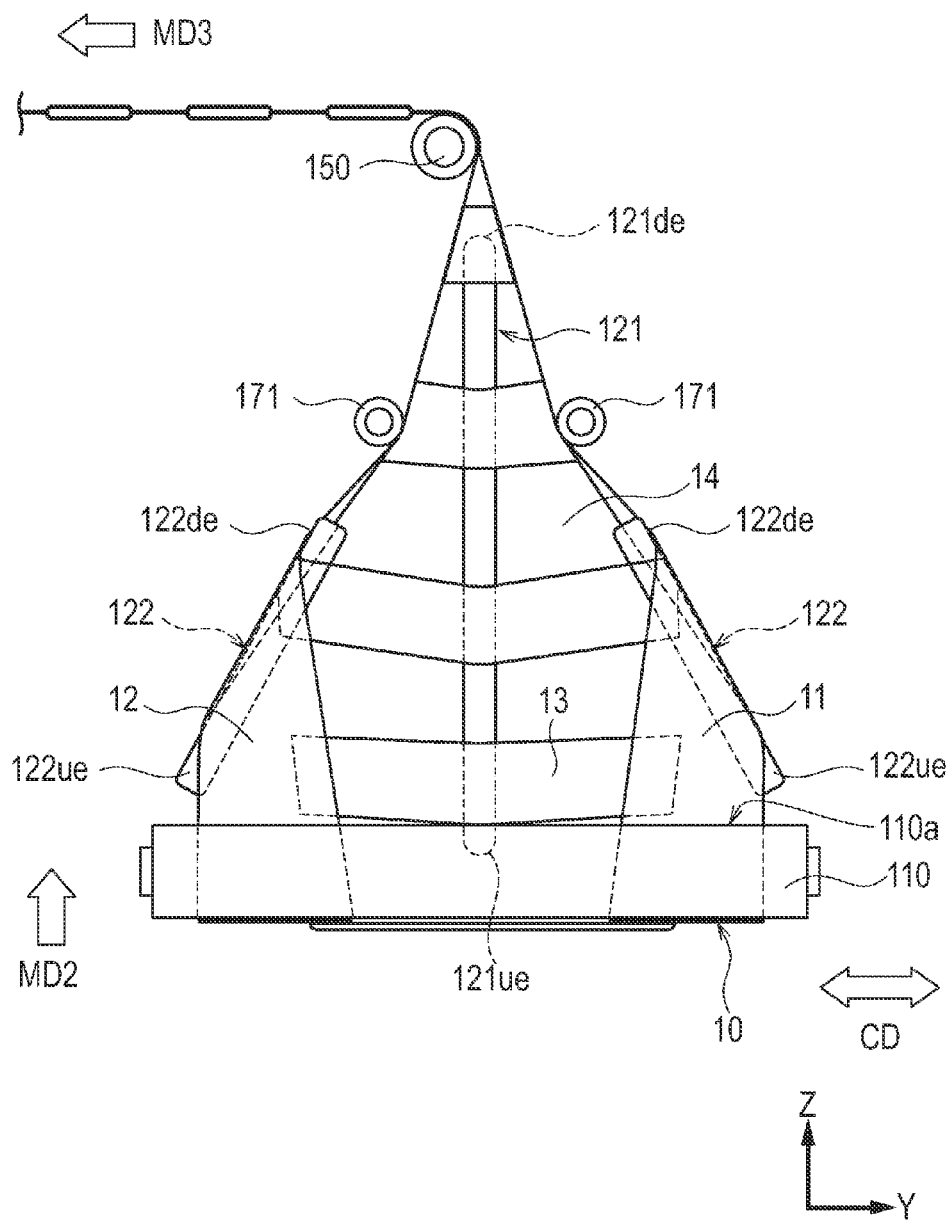
FIG. 3 is a front view showing the folding unit 120 according to the embodiment of the present invention.

FIG. 2 is a side view of the folding unit 120. FIG. 3 is a front view of the folding unit 120. As shown in FIGS. 2 and 3, the folding unit 120 has the central guiding unit 121 and the pair of side guiding units 122 provided in the sides of the central guiding unit, respectively.

The central guiding unit 121 extends in the direction MD2 (direction Z). As described above, the central guiding unit 121 is a rod shaped member, and a part of the central guiding unit 121, positioned upstream, that is, a part positioned at the folding base unit 110 side is in an arc-shape when viewed on the face XZ (see, FIG. 2). Therefore, the central guiding unit 121 is provided such that as it extends downstream, side in the conveyance direction, a distance from the front waistline portion 11 and the rear waistline portion becomes longer.

Further, the central guiding unit 121 comes in contact with the plurality of crotch portion 13 at the same time so as to extend across the plurality of leg-hole openings 14. A starting upstream end 121*ue* positioned upstream of the central guiding unit 121 is positioned upstream (a lower side) of an upper end 110*a* of the folding base unit 110. Further, a downstream end downstream from the central guiding unit 121 extends up to the vicinity of the superimposing roller 150.

The side guiding units 122 are provided laterally from the central guiding unit 121, respectively. The side guiding unit 122 is different from the central guiding unit 121 in that the side guiding unit 122 is in a linear shape when viewed on the face XZ (see, FIG. 2). The side guiding unit 122 is about half the length of the central guiding unit 121.

The side guiding units 122 are provided away from the central guiding unit 121. Downstream ends 122*de* downstream from the side guiding units 122 are positioned upstream from the downstream end 121*de* of the central guiding unit 121. On the other hand, upstream ends 122*ue* upstream from the side guiding units 122 are positioned downstream (an upper side) of the upper end 110*a* of the folding base unit 110. Further, the downstream ends 122*de* approach closer to the central guiding unit 121, as compared with the upstream ends 122*ue*. That is, the side guiding units 122 are disposed by being tilted such that an interval therebetween becomes shorter as they extend downstream.

The downstream ends 122*de* come in contact with the crotch portion 13 only. The side guiding units 122 are disposed by being tilted so as to come in contact with at least two of the crotch portions 13 at the same time. On the other hand, each of the upstream ends 122*ue* and its vicinity come in contact with the front waistline portion 11 or the rear waistline portion 12 only.

The automatic positioning mechanism 170 is provided between the downstream ends 122*de* of the side guiding units 122 and the downstream end 121*de* of the central guiding unit 121. The automatic positioning mechanism 170 includes a positioning roller 171 and an actuator 172.

The positioning roller 171 rotates in contact with one face (the front waistline portion 11 or the rear waistline portion 12) of the continuous web 10. The actuator 172 shifts the positioning roller 171 in a shaft center direction of the positioning roller 171 (see, FIG. 2). Note that ordinary products capable of performing revolving motions can be used as the actuator 172.

The positioning roller 171 is provided in a position at an inner side of extended lines EL passing through a part of the side guiding units 122, with which the continuous web 10 comes in contact (see, FIG. 4), so as to approach the central guiding unit 121, or alternatively, the positioning roller 171 is provided in a position at the outer side so as to be separated away from the central guiding unit 121. Accordingly, the positioning roller 171 can certainly come in contact with the continuous web 10.

The actuator 172 operates based on signals from a position detecting mechanism, not shown, which detects a position of the side edge of the continuous web 10. Note that the position detecting mechanism is capable to use a position detecting sensor with use of infrared rays, a laser, or the like.

When the positioning roller 171 is shifted in the shaft center direction D1 by the actuator 172, a position of the side edge of the front waistline portion 11 or the rear waistline portion 12 based on the central guiding unit 121 is changed, thereby making it possible to perform positioning of the side edge of the folded continuous web 10.

Figure 4:
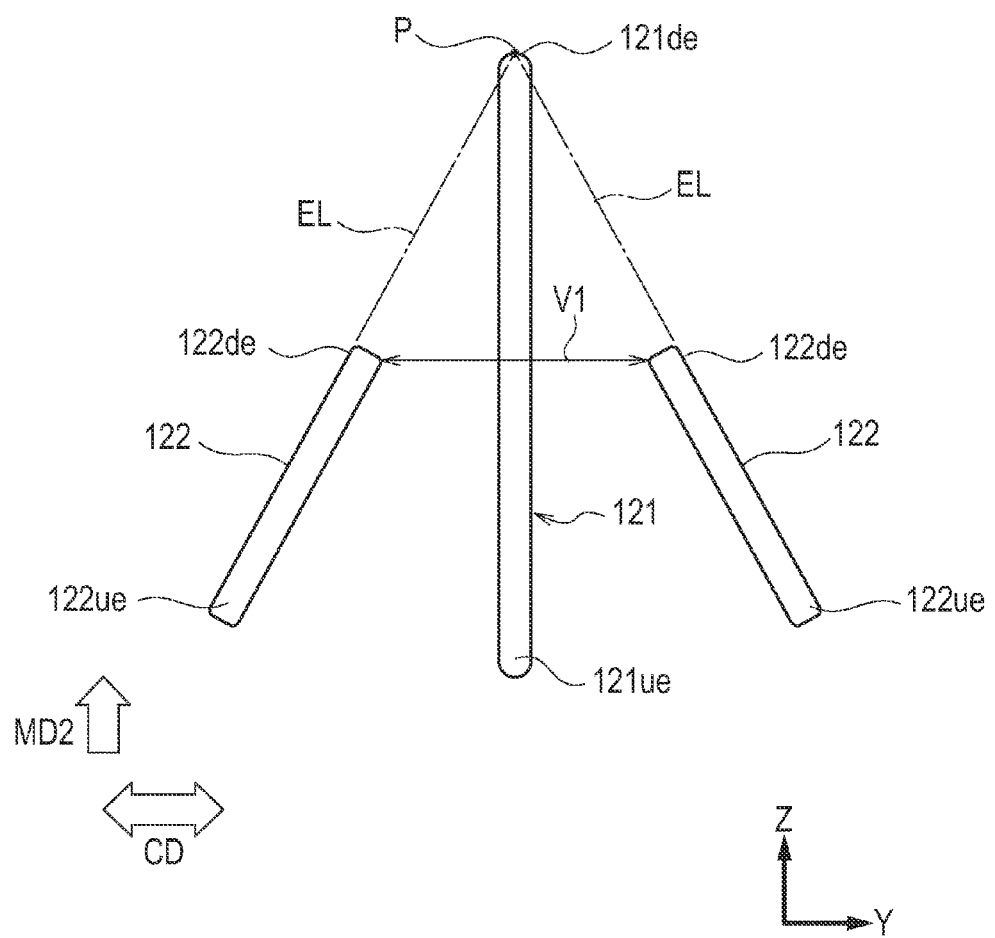
FIG. 4 is a view showing arrangement of a central guiding unit 121 and side guiding units 122 according to the embodiment of the present invention.

FIG. 4 shows the arrangement of the central guiding unit 121 and the side guiding units 122. As shown in FIG. 4, these units are provided such that each of the extended lines EL along contact parts 122*a* in which the side guiding units 122 come in contact with the continuous web 10 crosses the central guiding unit 121, when viewed in the direction (direction X) orthogonal to the face (face YZ) of the continuous web 10 to be conveyed in the direction MD2. In the present embodiment, an intersection point P between the extended lines EL and the central guiding unit 121 is positioned in the downstream end 121*de*.

Further, an interval V1 between the pair of side guiding units 122 becomes shorter as they extend downstream. Note that it is preferable that the interval V1 be about ¼ to ½ of the width in the crossing direction (CD) of the leg-hole opening 14.

(3) Modification

The folding unit 120 described above may be altered in the following ways. FIGS. 5(*a*) and 5(*b*) are views each showing folding units 120A, 120B according to a modification of the present invention.

As shown in FIG. 5(*a*), the folding unit 120A has a connecting unit 123 configured to connect the central guiding unit 121 and the side guiding units 122. The connecting unit 123 can be configured with use of a plate shaped member.

Further, as shown in FIG. 5(*b*), the folding unit 120B has the side guiding units 122 which are disposed by being tilted more than those of the folding unit 120. Therefore, the intersection point P is positioned away from the vicinity of the downstream end 121*de*. However, such arrangement of the side guiding unit 122 that the intersection point P is positioned downstream of the downstream end 121*de* is not preferable from the standpoint that the continuous web 10 is certainly folded.

The folding unit can be selected from the folding unit 120A shown in FIG. 5(*a*) and the folding unit 120B shown in FIG. 5(*b*), according to size, material, or conveyance speed of the continuous web 10, installation space of the processing device 100, or the like. For example, in a case of selecting the folding unit 120B, the continuous web 10 can be folded while saving space in the conveyance direction (direction MD2) required for the folding unit 120B.

According to the processing device 100 described above, the interval V1 between the pair of side guiding units 122 becomes shorter as they extend downstream. Further, the downstream ends 122*de* of the side guiding units 122 are positioned upstream from the downstream end 121*de* of the central guiding unit 121. Yet further, the superimposing roller 150 superimposes the front waistline portion 11 and the rear waistline portion, downstream from the side guiding units 122.

Therefore, a folding reference for the continuous web 10 is set in the side guiding units 122 and the superimposing roller 150. Further, with respect to the crotch portion 13 in which the leg-hole openings 14 are formed alternatingly, a folding position is determined so as to extend along the aforementioned folding reference. The central guiding unit 121 is provided along the crotch portion 13, between the pair of side guiding units 122. Further, the downstream ends 122*de* of the side guiding units 122 are positioned upstream of the downstream end 121*de* of the central guiding unit 121.

Specifically, the side guiding units 122 are terminated in the middle of folding of the continuous web 10, so that the folding unit 120 can fold the continuous web 10 in two without being affected by the leg-hole openings 14, and therefore, the front waistline portion 11 and the rear waistline portion 12 can be superimposed without being misaligned. Further, according to the processing device 100, in a case where the continuous web 10 is not folded while being conveyed in the horizontal direction, that is, not folded on the face XY, but is folded while being conveyed in the vertical direction, that is, folded on the face YZ, the effect of gravity can be discounted and a manufacturing line can be configured in a relatively small space.

Note that, other than the aforementioned prior art document (Japanese Patent Publication No. 2003-38566), a continuous web processing device disclosed in WO01/72237, for example, has been known. This processing device folds in two a web having no leg-hole openings, by using a triangular panel in which the apex is positioned downstream. Supposing the web having the leg-hole openings formed therein is folded in two by using such a triangular panel, the waistline portion of the continuous web 10 comes in contact with an oblique side part of the triangular panel first. Subsequently, the triangular panel comes in contact with the crotch portion. However, the triangular panel comes in contact with the crotch portion while crossing the leg-hole opening, thereby causing a problem that a folding position is not stabilized.

In the present embodiment, the extended lines EL along the contact parts 122*a* in which the side guiding units 122 come in contact with the continuous web 10 are provided so as to cross the central guiding unit 121. Therefore, in the folding unit 120, the region unaffected by the leg-hole openings 14 is increased, thereby further ensuring that the superimposition between the front waistline portion 11 and the rear waistline portion 12 is prevented from becoming unstable.

In the present embodiment, the side guiding units 122 are provided away from the central guiding unit 121. Therefore, in the folding unit 120, the area unaffected by the leg-hole openings 14 is increased, thereby further ensuring that the superimposition between the front waistline portion 11 and the rear waistline portion 12 is prevented from becoming unstable.

In the present embodiment, the upstream end 121*ue* of the central guiding unit 121 is positioned upstream from the upstream ends 122*ue* of the side guiding units 122. Therefore, when determining the folding reference of the continuous web 10, the central guiding unit 121 can avoid the effect of the leg-hole openings 14 formed alternatingly. That is, it is possible to further ensure that the superimposition between the front waistline portion 11 and the rear waistline portion 12 is prevented from becoming unstable.

In the present embodiment, the downstream ends 122*de* of the side guiding units 122 come in contact with the crotch portion 13 only. Further, the side guiding units 122 are disposed so as to come in contact with at least two of the crotch portions at the same time. Therefore, the effect of the leg-hole openings 14 formed alternatingly can be reduced. That is, it is possible to further ensure that the superimposition between the front waistline portion 11 and the rear waistline portion 12 is prevented from becoming unstable.

In the present embodiment, the superimposing roller 150 changes the conveyance direction of the continuous web 10 in which the front waistline portion 11 and the rear waistline portion 12 are superimposed on each other, from the MD2 to the MD3 orthogonal to the MD2. That is, on the layout of the processing device 100, the conveyance direction of the continuous web 10 conveyed in the vertical direction (MD2) is changed, so that the process for making the conveyance direction of the continuous web 10 correspond to the conveyance direction of other device can be omitted, and the installation space of manufacturing related facilities can be saved.

In the present embodiment, the automatic positioning mechanism 170 configured to adjust a position of one face (the front waistline portion 11 or the rear waistline portion 12) of the folded continuous web 10 is provided between the downstream ends 122*de* of the side guiding units 122 and the downstream end 121*de* of the central guiding unit 121. Therefore, even in a case where a folding position of the continuous web 10 adjusted by the side guiding units 122 is misaligned, the folding position can be corrected downstream from the side guiding units 122.

(4) Other Embodiment

So far, the present invention is disclosed through the above embodiments. However, it should not be interpreted that the statements and drawings configuring a part of the present disclosure limit the present invention. From this disclosure, a variety of alternate embodiments, examples, and applicable techniques will become apparent to one skilled in the art.

For example, in the above-described embodiments, the folding unit 120 folds in two the continuous web 10 to be conveyed in the vertical direction. However, the folding unit 120 may fold the web conveyed in the horizontal direction. Further, in the above-described embodiment, the conveyance direction of the continuous web 10 is changed by 90 degrees using the superimposing roller 150. However, a mechanism for twisting the continuous web 10 by 90 degrees may be used. In this case, such a mechanism has only to include a function as a superimposing unit for the front waistline portion 11 and the rear waistline portion 12.

In the above-described embodiments, the upstream end 121*ue* of the central guiding unit 121 is positioned upstream (a lower side) of the upstream ends 122*ue* of the side guiding units 122. However, positions of the upstream ends 121*ue*, 122*ue* may be different from those in the above-described embodiments. Further, positions of the pair of side guiding units 122 may not necessarily be symmetrical.

In the above-described embodiments, the folding base unit 110 is a cylindrical bar shaped member. However, the folding base unit 110 may be in a different shape (such as a curved plate form or the like) as long as it is capable of functioning as a base for folding the continuous web 10.

As described above, needless to say, the present invention includes various embodiments and the like not described here. Therefore, the technical range of the present invention is to be defined only by the inventive specific matter according to the adequate claims from the above description.

The entire contents of Japanese Patent Application No. 2010-069799 (filed on Mar. 25, 2010) are incorporated in the present specification by reference.

INDUSTRIAL APPLICABILITY

According to the present invention, it is possible to provide a continuous web processing device, by which in a case where a continuous web having a front waistline portion, a rear waistline portion, and crotch portion having leg-hole openings formed therein alternatingly is folded in two while being conveyed, a quality of products can be prevented from deteriorating due to the fact that superimposition between the front waistline portion and the rear waistline portion becomes unstable.

EXPLANATION OF REFERENCE NUMERAL

10 . . . continuous web, 11 . . . front waistline portion, 12 . . . rear waistline portion, 13 . . . crotch portion, 14 . . . leg-hole opening, 100 . . . processing device, 110 . . . folding base unit, 120 . . . folding unit, 121 . . . central guiding unit, 121*de* . . . downstream end, 121*ue* . . . upstream end, 122 . . . side guiding unit, 122*a* . . . contact part, 122*de* . . . downstream end, 122*ue* . . . upstream end, 150 . . . superimposing roller, 170 . . . automatic positioning mechanism, 171 . . . positioning roller, 172 . . . actuator

The invention claimed is:

1. A continuous web processing device configured to convey a continuous web having a front waistline portion, a rear waistline portion, and a crotch portion, while superimposing the front waistline portion and the rear waistline portion, the crotch portion being formed between the front waistline portion and the rear waistline portion and having leg-hole openings formed in the crotch portion alternatingly in a conveyance direction, the continuous web processing device comprising:

a folding base unit configured to come in contact with one face of the continuous web and change the conveyance direction of the continuous web from a first conveyance direction to a second conveyance direction in which alignments of the first conveyance direction and the second conveyance direction differ by approximately 90 degrees; and a folding unit configured to superimpose the front waistline portion and the rear waistline portion and to fold the continuous web in two about a center of the crotch portion, wherein:

the folding unit has:

a central guiding unit configured to extend in the second conveyance direction downstream from the folding base unit, and to come in contact with the crotch portion;

two side guiding units with one of the two side guiding units provided on each of opposite sides of the central guiding unit transverse to the second conveyance direction and extending in the second conveyance direction at least partially alongside the central guiding unit and being configured to come in contact with the front waistline portion and the rear waistline portion; and a superimposing unit configured to superimpose the front waistline unit and the rear waistline unit;

an interval between the two side guiding units becomes shorter along lengths thereof as the side guiding units extend downstream in the second conveyance direction;

downstream ends of the side guiding units downstream in the second conveyance direction are positioned upstream from a downstream end downstream of the central guiding unit in the second conveyance direction; and the superimposing unit superimposes the front waistline portion and the rear waistline portion, downstream from the side guiding units, wherein extended lines along parts in which the side guiding units come in contact with the continuous web are provided so as to cross the central guiding unit, when viewed in a direction orthogonal to the face of the continuous web conveyed in the second conveyance direction, wherein an upstream end of the central guiding unit is positioned upstream from upstream ends of the side guiding units, in the second conveyance direction.

2. The continuous web processing device according to claim 1, wherein the side guiding units not in contact with the central guiding unit.

3. The continuous web processing device according to claim 2, wherein the folding unit superimposes the front waistline portion and the rear waistline portion of the continuous web conveyed in a vertical direction.

4. The continuous web processing device according to claim 1, wherein the folding unit superimposes the front waistline portion and the rear waistline portion of the continuous web conveyed in a vertical direction.

5. The continuous web processing device according to claim 4, wherein when viewed in the direction orthogonal to the face of the continuous web conveyed in the second conveyance direction, the superimposing unit changes the conveyance direction of the continuous web having the front waistline portion and the rear waistline portion superimposed on each other, from the second conveyance direction to a direction orthogonal to the second conveyance direction.

6. The continuous web processing device according to claim 1, wherein:

the folding unit has an automatic positioning mechanism configured to adjust a position of the continuous web; and the automatic positioning mechanism is provided between the downstream ends of the side guiding units and the downstream end of the central guiding unit.

* * * * *